US010493224B2

(12) United States Patent
Meredith et al.

(10) Patent No.: US 10,493,224 B2
(45) Date of Patent: Dec. 3, 2019

(54) APPARATUS AND METHOD FOR IMPROVING AN ARTIFICIAL RESPIRATOR

(71) Applicants: AT&T INTELLECTUAL PROPERTY I, L.P., Atlanta, GA (US); AT&T MOBILITY II LLC, Atlanta, GA (US)

(72) Inventors: Sheldon K. Meredith, Roswell, GA (US); William Cottrill, Canton, GA (US); Brandon B. Hilliard, Woodstock, GA (US)

(73) Assignees: AT&T INTELLECTUAL PROPERTY I, L.P., Atlanta, GA (US); AT&T MOBILITY II LLC, Atlanta, GA (US)

( * ) Notice: Subject to any disclaimer, the term of this patent is extended or adjusted under 35 U.S.C. 154(b) by 1009 days.

(21) Appl. No.: 14/985,709

(22) Filed: Dec. 31, 2015

(65) Prior Publication Data

US 2017/0189631 A1    Jul. 6, 2017

(51) Int. Cl.
*A61M 16/06* (2006.01)
*A61M 16/00* (2006.01)

(52) U.S. Cl.
CPC ...... *A61M 16/0051* (2013.01); *A61M 16/024* (2017.08); *A61M 2205/13* (2013.01); *A61M 2205/3368* (2013.01); *A61M 2205/3375* (2013.01); *A61M 2205/3553* (2013.01); *A61M 2205/3561* (2013.01); *A61M 2205/3576* (2013.01); *A61M 2205/50* (2013.01)

(58) Field of Classification Search
CPC ....... A62B 18/08; A62B 18/02; A62B 18/025; A62B 7/00; A62B 7/02; A62B 7/14; A61M 16/0051; A61M 16/024; A61M 16/06; A61M 16/022; A61F 9/06; A61B 5/6831

See application file for complete search history.

(56) References Cited

U.S. PATENT DOCUMENTS

| 6,240,921 B1 | 6/2001 | Brydon et al. |
| 7,770,578 B2 | 8/2010 | Estes et al. |
| 8,311,645 B2 | 11/2012 | Bolea et al. |

(Continued)

FOREIGN PATENT DOCUMENTS

CN    202010334    10/2011

*Primary Examiner* — Tan-Uyen T Ho
*Assistant Examiner* — Margaret M Luarca
(74) *Attorney, Agent, or Firm* — Akerman LLP; Michael K. Dixon; Mammen (Roy) P. Zachariah, Jr.

(57) ABSTRACT

A system for improving an artificial respirator is disclosed. In particular, the system may be utilized to improve the quality of life of a user that utilizes an artificial respirator and to improve the quality of life of a caregiver of the user. In order to do so, the system may include an apparatus that suspends or activates one or more functions of the artificial respirator based on various conditions. As an example, if the system detects a threshold change in tension associated with a band supporting a respiration mask positioned on the user, the system may suspend a function of the artificial respirator. Similarly, if the system detects a temperature reading outside a temperature range, detects a unique sequence of inputs, detects a threshold distance between the user and the respiration mask, or detects other conditions, the system may suspend a function of the artificial respirator.

20 Claims, 3 Drawing Sheets

(56) References Cited

U.S. PATENT DOCUMENTS

| | | | |
|---|---|---|---|
| 8,356,594 B2 | 1/2013 | Ujhazy et al. | |
| 8,517,014 B2 | 8/2013 | Farrell et al. | |
| 8,744,589 B2 | 6/2014 | Bolea et al. | |
| 9,155,919 B2 | 10/2015 | Huh | |
| 2003/0189492 A1* | 10/2003 | Harvie | A61M 16/0051 |
| | | | 340/573.1 |
| 2011/0108041 A1 | 5/2011 | Sather et al. | |
| 2013/0199523 A1 | 8/2013 | Chen | |
| 2013/0276785 A1 | 10/2013 | Melker et al. | |
| 2014/0014110 A1 | 1/2014 | Adams | |
| 2015/0101600 A1 | 4/2015 | Miller et al. | |
| 2016/0193437 A1* | 7/2016 | Bao | G16H 40/63 |
| | | | 128/203.14 |
| 2017/0291001 A1* | 10/2017 | Rosenblatt | A61B 1/05 |
| 2017/0361045 A1* | 12/2017 | Fu | A61M 16/0683 |

* cited by examiner

APPARATUS AND METHOD FOR IMPROVING AN ARTIFICIAL RESPIRATOR

FIELD OF THE INVENTION

The present application relates to artificial respirator technologies, network communication technologies, controller technologies, and mobile device technologies, and more particularly, to a system, apparatus, and method for improving an artificial respirator.

BACKGROUND

In today's society, an ever-increasing number of individuals worldwide are suffering from various types of debilitating diseases and conditions. For example, in the United States alone, there are over 30,000 sufferers of amyotrophic lateral sclerosis (ALS). Additionally, a multitude of other individuals are also suffering from other diseases and conditions that affect the respiratory functions of individuals. Such diseases and conditions include, but are not limited to, lung cancer, bronchitis, chronic obstructive pulmonary disease (COPD), asthma, upper respiratory infections, lower respiratory infections, and various types of inflammatory diseases. Individuals suffering from such diseases and conditions may lose control of their diaphragms, have reduced breathing capabilities, have reduced lung function, have other lasting physical impairments, or any combination thereof. As a result, many of the individuals suffering from such diseases and conditions often require the use of artificial respirators to provide additional supporting air pressure and to facilitate and restore normal breathing function.

While current artificial respirators provide many benefits, current artificial respirators typically have loud alarms that constantly go off any time the air pressure detected is anomalous. Additionally, the machines and pumps utilized to provide air pressure variation and oxygen injection are generally very noisy as well. The noises created by alarms and the machines providing air pressure variation and oxygen injection not only have to be tolerated by the individual using the artificial respirator, but also by any caregivers. Until late stages of disease, such caregivers are typically family members of the individual using the artificial respirator. While professional caregivers are available, often times families cannot afford to have professional caregivers rendering any care at their homes. Additionally, caregivers often have varying abilities to tolerate the constant noise of the general operation of artificial respirators and the sounds generated by artificial respirator alarms. Furthermore, there are often instances where the individual using the artificial respirator needs to remove the respiration mask of the artificial respirator temporarily, such as when the individual needs to speak, consume food, go to the restroom, answer the door, or take a phone call. When the respiration mask is removed from the mouth of the individual, the added noise of the air movement through the mask is often quite loud. The loud noise generated by the removed respiration mask often causes substantial interruption and disturbance to others in located in the vicinity of the mask and user. For example, the noises generated by the mask may interrupt others that are watching television, talking on the phone, or trying to sleep. As a result, current artificial respirator technologies may be enhanced so as to provide a better quality of life to users of artificial respirators and to their caregivers, to provide improved functionality and features, and to provide improved ease-of-use.

SUMMARY

A system, an apparatus, and accompanying methods for improving an artificial respirator are disclosed. In particular, the system, apparatus, and methods improve the operation of an artificial respirator, such as by enabling a user to manually and remotely turn the artificial respirator on or off, or to suspend or reactivate various functions of the artificial respirator. Additionally, upon the detection of various conditions, the system, apparatus, and methods may also allow for the automatic suspension and/or reactivation of functions of the artificial respirator. Furthermore, failsafe mechanisms are provided that avoid unintentional suspension of various functions of the artificial respirator. In order to accomplish the foregoing, the system, apparatus, and methods may include providing multiple improvements to traditional artificial respirators. As an initial example, the system, apparatus, and methods may be configured to allow, such as when a respiration mask is removed, for the configuration of the artificial respirator to suspend or reduce the air pressure action of the machine for a period of time. Detection of the removal of the mask from the user may be performed by detecting a threshold change in tension in one or more bands or straps supporting the respiration mask on the head and mouth of the user.

As another example, the user may be provided with a remote control device, which may be mounted to the respiration mask, neck-worn by the user, wrist-worn by the user, or otherwise positioned on the user so as to allow the user to temporarily suspend the air pressure action of the artificial respirator and/or activate the air pressure action of the artificial respirator. In certain embodiments, such a remote control device may be peered to the artificial respirator to ensure that there is no confusion between other similar devices. In certain embodiments, the remote control device may include one or more input devices that may be utilized to input a temporal sequence to suspend and/or activate functions of the artificial respirator. With such abilities, the user may suspend operation of the artificial respirator intentionally for their own needs or in support of others, such as when others need to talk on the phone without background noise for a few minutes. In certain embodiments, whenever operation of the artificial respirator is manually or automatically suspended, the system, apparatus, and methods may reactivate the operation of the artificial respirator after a prescribed and/or configured duration. As a result, in the uncommon situation when the tension measurements on the bands or straps or the input devices on the remote control device provide incorrect control signals and the user is manually unable to press the buttons on the remote control device, the user will not be left without air pressure to the respiration mask, such as for a life-threatening duration. To further enhance this failsafe mechanism, when the air pressure operation of the artificial respirator is in a suspended state, the air pressure operation may be activated for a few cycles during the suspension period.

As a further example, the system, apparatus, and methods may include detecting the presence of the user with respect to the respiration mask of the artificial respirator. If the user wears a near-field communication (NFC) device, the NFC device may be detected by a similar NFC device or transceiver in the respiration mask. When the distance between the NFC device worn by the user and the NFC device or transceiver in the respiration mask exceeds a threshold, one or more functions of the artificial respirator may be suspended. The suspension action may be overridden by the user, such as by using the remote control device or even by using an application executing on a mobile device of the user. In this example, the system, apparatus, and methods may allow the user to simply remove the respiration mask and move away from the mask in order for the air pressure action to be suspended. As yet another example, the system, apparatus, and methods may include utilizing temperature detection from various positions on the respiration mask to detect contact with the user's skin. Multiple temperature sensors may obviate the potential that a single sensor is temporarily not in contact with the user's skin due to contortion of the respiration mask. In certain embodiments, the temperature sensors may work in concert with a NFC device to conduct an aggregate decision process. Such sensors may also record temperature measurements over time and relay the temperature measurements to a remote device or application to monitor the user's temperature and to even set alarms.

In yet a further example, the system, apparatus, and methods may include enabling the user to speak to others without the user having to remove the respiration mask from his or her head and/or mouth. In such a scenario, the respiration mask may include an electronic switch that may be switched to temporarily suspend air pressure, activate a microphone on the inside surface of the respiration mask, and activate a speaker positioned on the outside surface of the respiration mask, such as on a side of the respiration mask. The activated microphone and speaker may enable the user to speak, such as on a smartphone, with other users without having to remove the respiration mask. In still a further example, the system, apparatus, and methods may include enabling alerts generated by the artificial respirator to be ramped up over time. For example, the back-pressure to the respiration mask may be detected, and, if the back-pressure is below a threshold, a low-volume beeping or other sound may be output at a first frequency or periodicity. If the back-pressure remains too low for a selected duration, the volume of the beeping or other sound may gradually be increased until eventually the sound is output at a target volume, frequency, and/or periodicity. Such functionality is particularly useful when compared to traditional artificial respirators, which often output an incessant, maximum-volume sound, when back-pressure measurements are too low.

The system, apparatus, and methods may further include utilizing wireless communication to notify a remote device or application of any suspension and/or activation of an operation of the artificial respirator. This may provide a caregiver located in a different location from the user with the ability to be aware that the operation of the artificial respirator has been manually or automatically suspended and/or activated. The wireless communication may be made via point-to-point communication, such as by utilizing short-range wireless protocols or by network connection, such as by a cellular or other mobile device. As a result, the system, apparatus, and methods enhance the quality of life of a user using an artificial respirator and enhance the quality of life of the caregiver of the user, while simultaneously providing increased functionality and features when compared to traditional artificial respirators.

In one embodiment, a system for improving an artificial respirator is disclosed. The system may include a memory that stores instructions and a processor that executes the instructions to perform various operations of the system. The system may perform an operation that includes receiving, during a first time period, a first tension measurement from a tension sensor positioned on a respiration mask. The first tension measurement may indicate the amount of tension in one or more bands that support the respiration mask while the respiration mask is positioned on a user, such as over the user's mouth. The system may then perform an operation that includes receiving, during a second time period, a second tension measurement from the tension sensor. The second tension measurement may indicate the tension in the one or more bands supporting the respiration mask during the second time period. Once the first and second tension measurements are received, the system may perform an operation that includes determining if a change in tension between the first tension measurement and the second tension measurement exceeds a first threshold value. If the change in tension between the first tension measurement and the second tension measurement exceeds the first threshold value, the system may perform an operation that includes suspending a function of an artificial respirator coupled to the respiration mask.

In another embodiment, a method for improving an artificial respirator is disclosed. The method may include utilizing a memory that stores instructions, and a processor that executes the instructions to perform the various functions of the method. The method may include receiving, during a first time period, a first tension measurement from a tension sensor positioned on a respiration mask. The first tension measurement may indicate tension in one or more bands that support the respiration mask while the respiration mask is positioned on a user, such as over the user's mouth. Additionally, the method may include receiving, during a second time period, a second tension measurement from the tension sensor. The second tension measurement may indicate the tension in the one or more bands supporting the respiration mask during the second time period. Furthermore, the method may include determining if a change in tension between the first tension measurement and the second tension measurement exceeds a first threshold value. Moreover, the method may include suspending, if the change in tension between the first tension measurement and the second tension measurement exceeds the first threshold value, a function of an artificial respirator coupled to the respiration mask.

According to yet another embodiment, a computer-readable device having instructions for improving an artificial respirator is provided. The computer instructions, which when loaded and executed by a processor, may cause the processor to perform operations including: receiving, during a first time period, a first tension measurement from a tension sensor positioned on a respiration mask, wherein the first tension measurement indicates tension in a band that supports the respiration mask while the respiration mask is positioned on a head of a user; receiving, during a second time period, a second tension measurement from the tension sensor, wherein the second tension measurement indicates tension in the band; determining if a change in tension between the first tension measurement and the second tension measurement exceeds a first threshold value; and suspending, if the change in tension between the first tension measurement and the second tension measurement exceeds the first threshold value, a function of an artificial respirator coupled to the respiration mask.

These and other features of the systems, apparatuses, and methods for improving an artificial respirator are described in the following detailed description, drawings, and appended claims.

BRIEF DESCRIPTION OF THE DRAWINGS

FIG. 3 is a flow diagram illustrating a sample method for improving an artificial respirator according to an embodiment of the present disclosure.

DETAILED DESCRIPTION OF THE INVENTION

Figure 1:
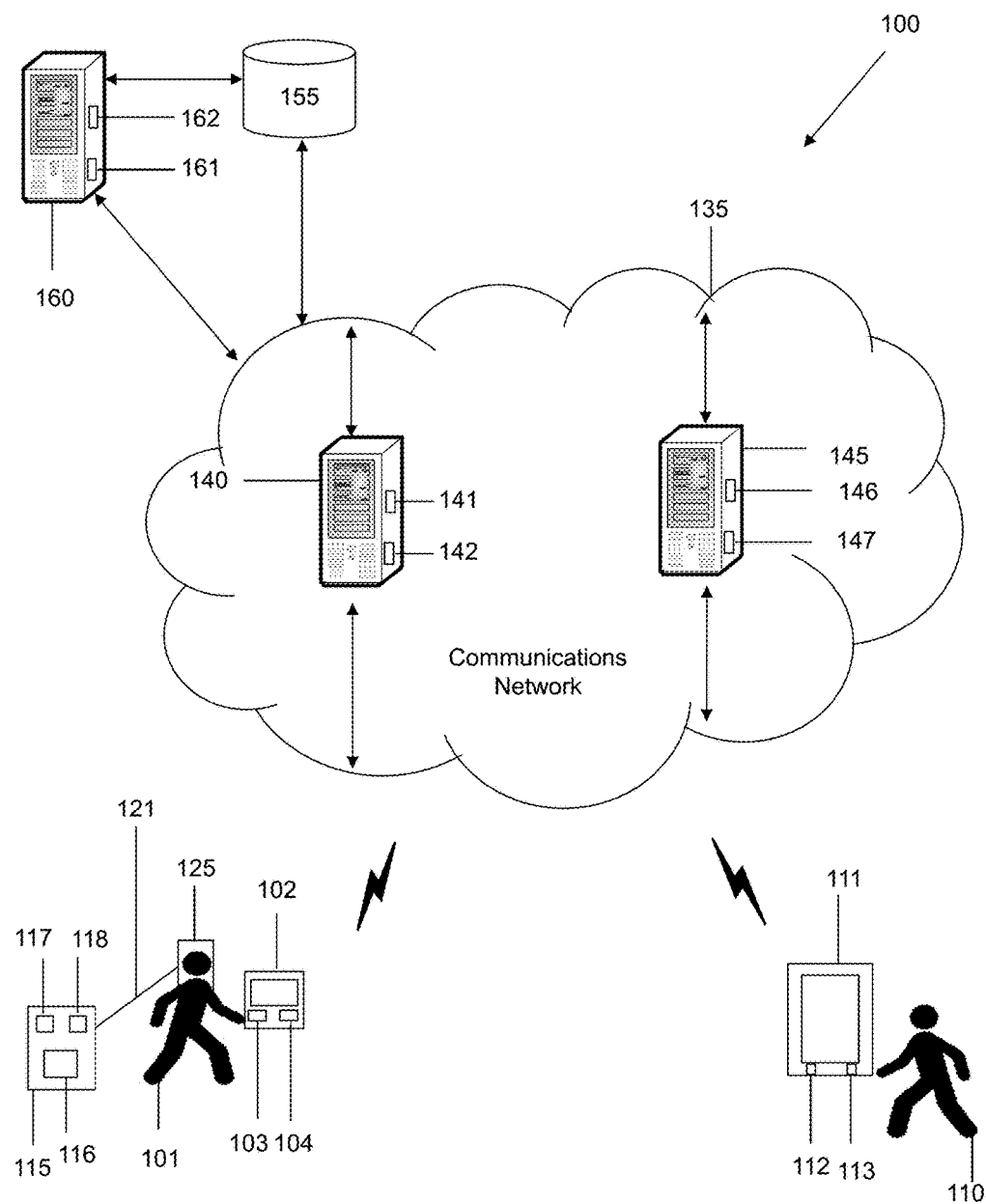
FIG. 1 is a schematic diagram of a system and apparatus for improving an artificial respirator according to an embodiment of the present disclosure.

A system 100, an apparatus 200, and accompanying methods for improving an artificial respirator 115 are disclosed. In particular, the system 100, apparatus 200, and methods improve the operation of an artificial respirator 115, such as by enabling a user (e.g. first user 101) to manually and remotely turn the artificial respirator 115 on or off, or to suspend or reactivate various functions of the artificial respirator 115. Additionally, upon the detection of one or more conditions, the system 100, apparatus 200, and methods may also allow for the automatic suspension and/or reactivation of functions of the artificial respirator 115. Furthermore, failsafe mechanisms are provided that prevent the unintentional suspension of various functions of the artificial respirator 115. In order to accomplish the foregoing, the system 100, apparatus 200, and methods may include providing multiple improvements to artificial respirators. As an example, the system 100, apparatus 200, and methods may be configured to allow, such as when a respiration unit 125 or respiration mask 126 is removed, for the configuration of the artificial respirator 115 to suspend or reduce the air pressure action of the artificial respirator machine for a period of time. The detection of the removal of the respiration unit 125 or mask 126 from the user may be performed by detecting a threshold change in tension in one or more bands 127 or straps supporting the respiration unit 125 or mask 126 on the head and mouth of the user.

As another example, the user may be provided with a remote control device (e.g. device controller 129 and/or peered-device controller 134), which may be mounted to the respiration mask 126, neck-worn by the user, wrist-worn by the user, or otherwise positioned on the user so as to allow the user to temporarily suspend the air pressure action of the artificial respirator 115 and/or to activate the air pressure action of the artificial respirator 115. In certain embodiments, such a remote control device may be peered to the artificial respirator 115 to ensure that there is no confusion between other similar devices. In certain embodiments, the remote control device may include one or more input devices that may be utilized to input a temporal sequence to suspend and/or activate functions of the artificial respirator 115. With such abilities, the user may suspend operation of the artificial respirator 115 intentionally for their own needs or in support of others. In certain embodiments, whenever the operation of the artificial respirator 115 is manually or automatically suspended, the system 100, apparatus 200, and methods may reactivate the operation of the artificial respirator 115 after a prescribed and/or configured duration. In the uncommon situation when the tension measurements on the bands 127 or straps or the input devices on the remote control device provide incorrect control signals and the user is manually unable to press the buttons on the remote control device, the user will not be left without air pressure to the respiration mask 126. As a further enhancement to this failsafe mechanism, when the air pressure operation of the artificial respirator 115 is in a suspended state, the air pressure operation may be activated for a few cycles during the suspension period.

As a further example, the system 100, apparatus 200, and methods may include detecting the presence of the user with respect to the respiration unit 125 or mask 126 of the artificial respirator 115. If the user wears a near-field communication (NFC) device 133, the NFC device 133 may be detected by a similar NFC device 130 or transceiver in the respiration mask 126. When the distance between the NFC device 133 worn by the user and the NFC device 130 or transceiver in the respiration mask 126 exceeds a threshold, one or more functions of the artificial respirator 115 may be suspended or reduced. The suspension action may be overridden by the user, such as by using the remote control device or even by using an application executing on a mobile device (e.g. first user device 102) of the user. In this example, the system 100, apparatus 200, and methods may allow the user to simply remove the respiration unit 125 or mask 126 and move away from the unit 125 or mask 126 in order for the air pressure action to be suspended. As yet another example, the system 100, apparatus 200, and methods may include utilizing temperature detection from various positions on the respiration mask to detect contact with the user's skin. Multiple temperature sensors 131 may obviate the potential that a single sensor 131 is temporarily not in contact with the user's skin due to contortion of the respiration unit 125 or mask 126. In certain embodiments, the temperature sensors 131 may work in concert with a NFC device 130 to conduct an aggregate decision process, such as a decision process relating to whether an alert should be generated and transmitted. Such sensors 131 may also record temperature measurements over time and relay the temperature measurements to a remote device or application to monitor the user's temperature and to even set alarms.

In yet a further example, the system 100, apparatus 200, and methods may include enabling the user to speak to others without the user having to remove the respiration unit 125 or mask 126 from the user's head and/or mouth. The respiration unit 125 or mask 126 may include an electronic switch 136 that may be switched to temporarily suspend air pressure and to activate a microphone/speaker 132 on the respiration unit 125 or mask 126. The activated microphone/speaker 132 may enable the user to speak, such as on a smartphone, with other users without having to remove the respiration unit 125 or mask 126. In still a further example, the system 100, apparatus 200, and methods may include enabling alerts generated by the artificial respirator 115 to be ramped up over time. For example, the back-pressure to the respiration mask 126 may be detected, and, if the back-pressure is below a threshold, a low-volume beeping or other sound may be output at a first frequency or periodicity. If the back-pressure remains too low for a selected duration, the volume of the beeping or other sound may gradually be increased until eventually the sound is output at a target volume, frequency, and/or periodicity.

The system 100, the apparatus 200, and methods may further include utilizing wireless communication to notify a remote device (e.g. servers 140, 145) or application of any suspension and/or activation of an operation of the artificial respirator 115. This may provide a caregiver (e.g. second user 110) located in a different location from the user with the knowledge that the operation of the artificial respirator has been manually or automatically suspended and/or activated. The wireless communication may be made via point-to-point communication, such as by utilizing short-range wireless protocols or by network connection, such as by a cellular or other mobile device. As a result, the system 100, the apparatus 200, and methods enhance the quality of life of a user using an artificial respirator 115 and enhance the quality of life of the caregiver of the user, while simultaneously providing increased functionality and features when compared to traditional artificial respirators.

Figure 2:
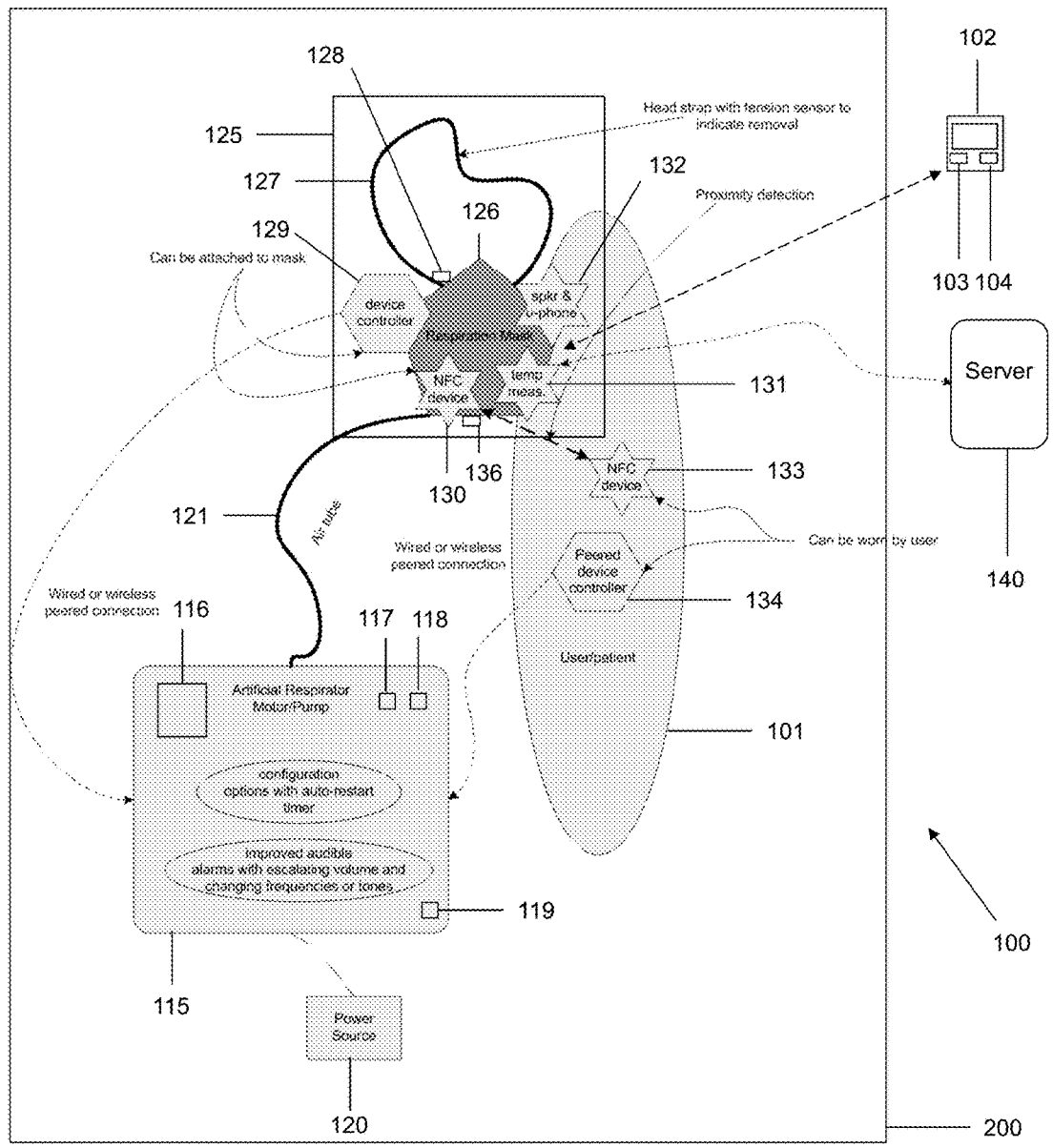
FIG. 2 is a schematic diagram illustrating additional components and functionality of the system and apparatus of FIG. 1.

As shown in FIGS. 1-2, a system 100 and apparatus 200 that improves an artificial respirator 115 is disclosed. The system 100 may be configured to support, but is not limited to supporting, healthcare services, IPTV services, digital video recorder services, cloud computing services, content delivery services, IP Multimedia Subsystem (IMS) services, satellite services, fiber services, telephone services, voice-over-internet protocol services (VoIP), voice-over-long-term-evolution (VoLTE) services, LTE services, software as a service (SaaS) applications, gaming applications and services, social media applications and services, operations management applications and services, productivity applications and services, mobile applications and services, and any other computing applications and services. The system may include a first user 101 that may require the use of an artificial respirator 115 to assist the first user 101 with respiration. The first user 101 may utilize a first user device 102 to control the artificial respirator 115, control the apparatus 200, control devices on the respiration mask 126, access data, access content, access services, transmit alerts, and/or to perform a variety of other functions. As an example, the first user 101 may utilize first user device 102 to transmit signals to the system 100 to activate and/or deactivate functions of the artificial respirator 115, perform any other operations, or any combination thereof.

In certain embodiments, the first user 101 may be a subscriber of a service provider that controls communications network 135, and the first user device 102 may be equipped for mobile communication. The first user device 102 may include a memory 103 that includes instructions, and a processor 104 that executes the instructions from the memory 103 to perform the various operations that are performed by the first user device 102. In certain embodiments, the processor 104 may be hardware, software, or a combination thereof. In certain embodiments, the first user device 102 may be a computer, a laptop, a set-top-box, a tablet device, a phablet, a server, a mobile device, a smartphone, a smart watch, or any other type of computing device. Illustratively, the first user device 102 is shown as a smartphone device in FIGS. 1-2. In certain embodiments, the first user device 102 may communicate with the artificial respirator 115, devices on the respiration mask 126, NFC devices 130, 133, the device controller 129, the peered-device controller 134, any of the devices in the system 100, or any combination thereof, by utilizing infrared radiation, radio frequency technologies, Bluetooth connectivity, Zig-Bee, Z-Wave, any type of wireless protocol, radio technologies, or any combination thereof.

The system may also include a second user 110 that may utilize a second user device 111 to also access data, content, and services, and to perform a variety of other functions. For example, the second user device 111 may be utilized by the second user 110 to transmit signals to request various types of measurements and data provided by the artificial respirator 115, the temperature sensors 131, the NFC devices 130, 133, the tension sensor 128, any other devices in the system 100, or any combination thereof. In certain embodiments, the second user 110 may be a subscriber of a service provider that controls communications network 135, and the second user device 111 may be equipped for mobile communication. In certain embodiments, the second user 110 may be a caregiver, such as, but not limited to, a family member of the first user 101, a physician, a nurse, or any combination thereof. The second user device 111 may include a memory 112 that includes instructions, and a processor 113 that executes the instructions from the memory 112 to perform the various operations that are performed by the second user device 111. In certain embodiments, the processor 113 may be hardware, software, or a combination thereof. Similar to the first user device 102, in certain embodiments, the second user device 111 may be a computer, a laptop, a tablet device, a phablet, a server, a mobile device, a smartphone, a smart watch, or any other type of computing device. Illustratively, the second user device 111 is shown as a tablet device in FIG. 1. In certain embodiments, the second user device 111 may communicate with the artificial respirator 115, devices on the respiration mask 126, NFC devices 130, 133, the device controller 129, the peered-device controller 134, the first user device 102, any of the devices in the system 100, or any combination thereof, by utilizing infrared radiation, radio frequency technologies, Bluetooth connectivity, ZigBee, Z-Wave, any type of wireless protocol, radio technologies, or any combination thereof.

In certain embodiments, the first and second user devices 102, 111 may have any number of software applications and/or application services stored and/or accessible thereon. For example, the first and second user devices 102, 111 may include healthcare-based applications, health monitoring applications, medical applications, applications for communicating with the artificial respirator 115, applications for communicating with any devices of the respiration unit 125 and/or respiration mask 126, cloud-based applications, VoIP applications, other types of phone-based applications, product-ordering applications, business applications, e-commerce applications, media streaming applications, content-based applications, media-editing applications, database applications, gaming applications, internet-based applications, browser applications, mobile applications, service-based applications, productivity applications, video applications, music applications, social media applications, any other type of applications, any types of application services, or a combination thereof. In certain embodiments, the software applications and services may include one or more graphical user interfaces so as to enable the first and second users 101, 110 to readily interact with the software applications. The software applications and services may also be utilized by the first and second users 101, 110 to interact with the any device in the system 100, any network in the system 100, or any combination thereof. In certain embodiments, the first and second user devices 102, 111 may include associated telephone numbers, device identities, or any other identifiers to uniquely identify the first and second user devices 102, 111.

In certain embodiments, the first and second user devices 102, 111 may have corresponding device profiles. In certain embodiments, each of the devices in the system 100 may have its own corresponding device profile. For example, the artificial respirator 115, the respiration unit 125, the respiration mask 126, the temperature sensors 131, the NFC devices 130, 133, and the device controller 129 may have their own device profiles. Information included in a device profile may include, but is not limited to, information specifically corresponding to the first and second user devices 102, 111, information identifying the types of devices that the first and second user devices 102, 111 are, information relating to how the first user 101 utilizes the first user device 102, information relating to how the second user 110 utilizes the second user device 111, information identifying what type of services and information the first user 101 and second user 110 are authorized to access, information indicating each type of component included in the first and second user devices 102, 111, information identifying the processing power, storage capacity, download capabilities, and upload capabilities associated with the first and second user devices 102, 111, any other information associated with the first and second user devices 102, 111, or any combination thereof. The device profiles may be made accessible to any device, network, or a combination thereof, in the system 100.

In addition to device profiles, the system 100 may also include user profiles. A user profile may be a profile corresponding to the first user 101, the second user 110, or any other user. For example, the first user's 101 profile may include information, such as, but not limited to, a name of the first user 101, the age of the first user 101, demographic information associated with the first user 101, information identifying the first user device 102, the types of services subscribed to by the first user 101, information identifying a location of the first user 101, information identifying the types of applications that the first user 101 utilizes, information identifying health conditions of the first user 101, information identifying configuration preferences for configuring the functionality of the artificial respirator 115, information identifying the types of alarms that the first user 101 likes to use with the artificial respirator 115, any other information, or any combination thereof. The user profiles may be stored directly on the first user device 102, the second user device 111, the database 155, on any other device in the system 100, or on any combination thereof. Additionally, the user profiles may be accessible by any device in the system 100, any network in the system 100, or a combination thereof.

The system 100 may include an artificial respirator 115, which may be utilized to provide and/or force air into the lungs of a user, such as first user 101. In particular, the artificial respirator 115 may be utilized to deliver oxygen to a user who may have impaired breathing capabilities or may be unable to breathe on his or her own. The artificial respirator 115 may have any of the components, functionality, and/or features of any traditional artificial respirator. Additionally, the artificial respirator 115 may include a motor/pump 116 that may be utilized to generate and pump air including oxygen with enough pressure so that the air may pass through the air tube 121, then through the respiration mask 126, and then into the first user's 101 lungs. The artificial respirator 115 may also include a memory 117 that includes instructions, and a processor 118 that executes the instructions from the memory 117 to perform the various operations that are performed by the artificial respirator 115. In certain embodiments, the processor 118 may be hardware, software, or a combination thereof. In certain embodiments, the artificial respirator 115 may also include a transceiver 119, which may be utilized to receive signals from any devices in the system 100 and/or transmit signals to any devices in the system 100. In further embodiments, the artificial respirator 115 may be powered by one or more power sources 120, such as, but not limited to, a battery power source, an electrical power source, a solar power source, any type of power source, or any combination thereof. Functions and/or operations of the artificial respirator 115 may include, but are not limited to, providing air at selected pressures, not providing air, providing air at a certain rate/cycle, varying the pressure at which air is provided, providing air according to a schedule, providing variable compositions of air including varying percentages of oxygen, outputting sounds (e.g. sounds that are outputted when the respiration mask 126 is removed from the head of the user or sounds that are outputted when back-pressure measurements are too low), outputting alerts, outputting alarms, functions performed by the motor/pump 116, functions performed by the transceiver 119, functions performed by the memory 117 and processor 118, any type of function performed by any type of artificial respirator, or any combination thereof.

The system 100 may also include a respiration unit 125 that may be coupled to the artificial respirator 115 via the air tube 121. The respiration unit 125 may receive air from the artificial respirator 115 via the air tube 121, and deliver the air to the first user 101 when the respiration unit 115 is positioned on the first user's 101 head and the respiration mask 126 covers the first user's 101 mouth. In certain embodiments, the respiration unit 125 may include a respiration mask 126, one or more bands 127 (or straps) that may be utilized to secure the respiration mask 126 to the first user's 101 head, one or more tension sensors 128 that may be utilized to provide tension measurements associated with tension in the bands 127, a device controller 129, an NFC device 130, one or more temperature sensors 131, a microphone/speaker 132, a switch 136, any other desired device, or any combination thereof.

The respiration mask 126 of the respiration unit 125 may be utilized to cover over the mouth of the first user 101 and form a seal over the mouth of the first user 101 so that air may be delivered to the first user 101 via the respiration mask 126. In certain embodiments, the respiration mask 126 may include any of the features, componentry, and functionality of a bag valve mask, any type of respiratory mask, or any combination thereof. The respiration mask 126 may be made of any suitable material, such as, but not limited to, plastic, rubber, any other material, or any combination thereof. The respiration mask 126 may be secured to the first user 101 via the bands 127 (or strap), which may be elastic. The first user 101 may place the bands 127 over and around his head to secure the respiration mask 126 in place and over his mouth. One or more tension sensors 128 may be placed at any location on the periphery of the respiration mask 126 and/or in proximity to the locations where the bands 127 connect to the respiration mask 126. The tension sensors 128 may generate and record tension measurements that occur when the bands 127 of the respiration unit 125 are stretched and/or contracted. For example, as the first user 101 removes the respiration mask 126 from the first user's 101 head the tension measurement associated with the bands 127 when they are stretched as the first user 101 removes the respiration mask 126 may be measured and obtained via the tension sensor 128. Similarly, when the first user 101 places the respiration mask 126 over his head to secure the respiration mask 126 over his mouth, the tension measurement associated with the contraction that occurs in the bands 127 may also be measured by the tension sensor 128. Any change in tension in the bands 127 may be measured by the tension sensor 128 and the tension measurements may be sent to any device in the system 100 for further analysis and processing.

The device controller 129 of the respiration unit 125 may be utilized to control the various devices and sensors of the respiration unit 125 and/or the artificial respirator 115. In certain embodiments, the device controller 129 may be mounted to the respiration mask 126, on other locations of the respiration unit 125, or on any other desired location. In certain embodiments, the device controller 129 may include any number of input devices, such as buttons or toggles devices, that may be depressed or switched to suspend the air pressure action (or other functions) of the artificial respirator 115 and/or activate the air pressure action of the artificial respirator 115. In certain embodiments, the device controller 129 may be paired with the artificial respirator 115 via a wired or wireless peered connection, which may be facilitated through the use of NFC communication technologies, infrared radiation, radio frequency technologies, Bluetooth connectivity, ZigBee, Z-Wave, any type of wireless protocol, radio technologies, or any combination thereof. The peering may be performed between the artificial respirator 115 and the device controller 129 to avoid any confusion between other similar devices. In certain embodiments, in order to suspend (or activate) a function of the artificial respirator 115, the input devices may need to be depressed or switched according to a predetermined temporal sequence to avoid accidental control of the artificial respirator 115. For example, in order to suspend the air pressure action provided by the artificial respirator, performing the temporal sequence of "tap, tap, pause for 1 second (or other desired timeframe), tap, tap" using a button of the device controller 129 may be required. Notably, any type of temporal or other sequence may be utilized to suspend or activate functions of the artificial respirator 115.

The respiration unit 125 may also include a NFC device 130, which may include a transceiver and/or any other componentry and features of a traditional NFC device. In certain embodiments, the NFC device 130 may be configured to utilize any set of communication protocols (e.g. NFC protocols or other protocols) to communicate with the artificial respirator 115, the respiration unit 125 (or any device of the respiration unit 125), the first user device 102, the second user device 111, the NFC device 133, the device controller 129, the peered-device controller 134, any other device in the system 100, or any combination thereof. In certain embodiments, the NFC device 130 may establish radio data communication with the first user device 102 and/or the second user device 111. The NFC device 130 may include NFC readers, tags, and/or any other NFC devices. In certain embodiments, the NFC device 130 may be positioned on the respiration mask 126, on other locations of the respiration unit 125, or on any other desired location. In certain embodiments, the NFC device 130 may be configured to determine the distance between the NFC device 130 and any other device in the system 100, such as NFC device 133. The NFC device 130 and/or the devices in the system 100 may be able to determine the distance based on the signal strength of a connection with a device in communication with the NFC device 130, based on any available distance measuring technique, or any combination thereof.

The respiration unit 125 may further include one or more temperature sensors 131, which may be configured to record and detect temperature measurements along various locations of interest on the respiration mask 126. For example, the temperature sensors 131 may take temperature measurements along the portions of the respiration mask 126 that seal around the first user's 101 skin on the first user's 101 face, nose, and/or mouth. The temperature measurements measured by the temperature sensors 131 may be sent to any device in the system 100 for processing and storage, and may be obtained over selected time intervals to determine trends or historical temperature readings for the first user 101 and respiration unit 125. In certain embodiments, if the temperature measurements are lower than a threshold temperature value (e.g. the first user's 102 body temperature), this may serve as an indication that the respiration mask 126 is not properly sealed onto the first user's 101 face and/or that the respiration mask 126 has been completely removed from the first user's 101 face. Similarly, if the temperature measurements are outside an expected temperature range, this may also indicate that the respiration mask 126 is not properly secured to the first user 101.

In certain embodiments, the respiration unit 125 may also include a microphone/speaker 132. The microphone of the microphone/speaker 132 may be transducer or sensor that converts inputted sounds, such as the first user's 101 speech or other sounds, into an electrical signal, which may then be processed by the speaker of the microphone/speaker 132 to output the sound. The sound outputted by the speaker of the microphone/speaker 132 may serve as an input to a microphone of the first user device 102, such as when the first user 101 is on a call with the second user 110. In certain embodiments, the microphone of the microphone/speaker 132 may be placed on the inside of the respiration mask 126 and the speaker may be placed on the outside of the respiration mask 126. In preferred embodiments, the speaker may be placed on either side on the outside of the respiration mask 126, so that the first user 101 may hold the first user device 102 by the first user's 101 head during a call and the speech output via the speaker may easily be picked up by the microphone of the first user device 102 so that the second user 110 that is communicating with the first user 101 may easily hear the first user's 101 speech. In certain embodiments, the microphone/speaker 132 may be activated and/or deactivated by toggling the switch 136, which may be located on the respiration unit 125 or at any other desired location on the apparatus 200. The toggling of the switch 136 may also be utilized to suspend and/or activate one or more functions of the artificial respirator 115 as well.

In certain embodiments, the system 100 may include a NFC device 133, which may include a transceiver and/or any other componentry and features of a traditional NFC device. In certain embodiments, the NFC device 133 may be configured to utilize any set of communication protocols (e.g. NFC protocols or other protocols) to communicate with the artificial respirator 115, the respiration unit 125 (or any device of the respiration unit 125), the first user device 102, the second user device 111, the NFC device 130, the device controller 129, the peered-device controller 134, any other device in the system 100, or any combination thereof. In certain embodiments, the NFC device 133 may establish radio data communication with the first user device 102 and/or the second user device 111. The NFC device 133 may include NFC readers, tags, and/or any other NFC devices. In certain embodiments, the NFC device 133 may be positioned on a necklace that may be worn by the first user 101, on the body of the first user 101, on clothing of the first user 101, on a neck-worn device, on the peered-device controller 134, or on any other desired location. In certain embodiments, the NFC device 133 may be configured to determine the distance between the NFC device 133 and any other device in the system 100, such as NFC device 130. The NFC device 133 and/or the devices in the system 100 may be able to determine the distance based on the signal strength of a connection with a device in communication with the NFC device 133, based on any available distance measuring technique, or any combination thereof.

In further embodiments, the system 100 may include a peered-device controller 134. As with the device controller 129, the peered-device controller 134 may be utilized to control the various devices and sensors of the respiration unit 125 and/or the artificial respirator 115. In certain embodiments, the peered-device controller 134 may be worn by the first user 101, positioned on a device of the first user 101, worn on clothing of the first user 101, or on any other desired location. In certain embodiments, the peered-device controller 134 may include any number of input devices, such as buttons or toggles devices, that may be depressed or switched to suspend the air pressure action of the artificial respirator 115 and/or activate the air pressure action of the artificial respirator 115. In certain embodiments, the peered-device controller 134 may be paired with the artificial respirator 115 via a wired or wireless peered connection, which may be facilitated through the use of NFC communication technologies, infrared radiation, radio frequency technologies, Bluetooth connectivity, ZigBee, Z-Wave, any type of wireless protocol, radio technologies, or any combination thereof. The peering may be performed between the artificial respirator 115 and peered-device controller 134 to avoid any confusion between other similar devices. In certain embodiments, in order to suspend (or activate) a function of the artificial respirator 115, the input devices may need to be depressed or switched according to a predetermined temporal sequence to avoid accidental control of the artificial respirator 115. For example, in order to suspend the air pressure action provided by the artificial respirator, performing the temporal sequence of "tap, tap, pause for 1 second (or other desired timeframe), tap, tap" using a button of the peered-device controller 134 may be required. Notably, any type of temporal or other sequence may be utilized to suspend or activate functions of the artificial respirator 115. The peered-device controller 134 may also peer with the NFC device 130 as well and may exchange any data of the system 100 with the NFC device 130.

The system 100 may also include a communications network 135. The communications network 135 of the system 100 may be configured to link each of the devices in the system 100 to one another. For example, the communications network 135 may be utilized by the first user device 102 to connect with other devices within or outside communications network 135. Additionally, the communications network 135 may be configured to transmit, generate, and receive any information and data traversing the system 100. In certain embodiments, the communications network 135 may include any number of servers, databases, or other componentry, and may be controlled by a service provider. In certain embodiments, the communications network 135 may be subscribed to by the first and second users 101, 110. The communications network 135 may also include and be connected to a radio access network, a cloud-computing network, an IMS network, a VoIP network, a VoLTE network, an LTE network, a wireless network, an Ethernet network, a fiber network, a satellite network, a broadband network, a cellular network, a private network, a cable network, the Internet, an internet protocol network, a multiprotocol label switching (MPLS) network, a content distribution network, an internet protocol television network, any network, or any combination thereof. Illustratively, servers 140, 145 are shown as being included within communications network 135. In certain embodiments, the communications network 135 may be part of a single autonomous system that is located in a particular geographic region, or be part of multiple autonomous systems that span several geographic regions.

In certain embodiments, the communications network 135 may be configured to deliver data, media content, and service using an internet protocol suite and by utilizing packet switching. The communications network 135 may provide the ability to stream data and content requested by the first and second users 101, 110, receive and/or transmit any data generated by the artificial respirator 115, receive and/or transmit any data generated by the respiration unit 125, receive and/or transmit any data generated by the tension sensors 128, receive and/or transmit any data generated by the temperature sensors 131, any data generated by any other device of the system 100, or any combination thereof. In certain embodiments, the communications network 135 may include any of the components and functionality found in traditional communication networks. In certain embodiments, the communications network 135 may include hardware components that include any of the functional features of a radio access network. The communications network 135 may be configured to provide cellular services (e.g. LTE services), any type of services, or any combination thereof. Additionally, the communications network 135 may include any of the functionality of a base station utilized in mobile communication networks. For example, the communications network 135 may include any number of antennae, transceivers, digital signal processors, control electronics, GPS receivers, electrical power sources, radio equipment, and electronics equipment to create a cell for the communications network 135. The communications network 135 may be configured to communicate with and receive content and data streams from any other network or system, or any combination thereof.

Notably, the functionality of the system 100 may be supported and executed by using any combination of the servers 140, 145, and 160. In certain embodiments, the server 140 may include a memory 141 that includes instructions, and a processor 142 that executes the instructions from the memory 141 to perform various operations that are performed by the server 140. The processor 142 may be hardware, software, or a combination thereof. Similarly, the server 145 may include a memory 146 that includes instructions, and a processor 147 that executes the instructions from the memory 146 to perform the various operations that are performed by the server 145. In certain embodiments, the servers 140, 145, and 160 may be network servers, routers, gateways, computers, mobile devices or any other suitable computing device. In certain embodiments, the servers 140, 145 may be communicatively linked to the communications network 135, any network, any device in the system 100, or any combination thereof.

The database 155 of the system 100 may be utilized to store and relay information that traverses the system 100, cache content that traverses the system 100, store data about each of the devices in the system 100 and perform any other typical functions of a database. In certain embodiments, the database 155 may be connected to or reside within the communications network 135, any other network, or a combination thereof. Additionally, the database 155, in certain embodiments, may serve as a data and content source for stored data and content that may be accessed by the communication network 135 so that the communication network 135 may obtain the data and content for the first and second users 101, 110 in an efficient and effective manner In certain embodiments, the database 155 may serve as a central repository for data and content and information requested by the first and second users 101, 110. Furthermore, the database 155 may include a processor and memory or be connected to a processor and memory to perform the various operation associated with the database 155.

In certain embodiments, the database 155 may be connected to servers 140, 145, 160, first user device 102, second user device 111, artificial respirator 115, respiration unit 125, NFC devices 130, 133, temperature sensor 131, tension sensor 128, device controller 129, peered-device controller 134, any other device, or any combination thereof. The database 155 may also store information and metadata obtained from the system 100, store media content, store metadata and other information associated with the first and second users 101, 110, store user profiles associated with the first and second users 101, 110, store device profiles associated with the first user device 102, the second user device 111, the artificial respirator 115, the respiration unit 125 and/or any other device in the system 100, store location information, store communications traversing the system 100, store user preferences, such as preferences relating to the operation of the artificial respirator 115, store information associated with any device or signal in the system 100, store information relating to patterns of usage relating to the first and second user devices 102, 111, store content, store different resolutions of media content, store service subscription information associated with services subscribed to by the first and second users 101, 110, store information utilized for identifying communications network 135, store tension measurements obtained from the tension sensor 128, store temperature measurements from the temperature sensors 131, store back-pressure measurements associated with back-pressure on the respiration mask 126, store breathing rate information, store input sequences for suspending or activating functions of the artificial respirator 115, store data identifying when and how often a function of the artificial respirator 115 was suspended and/or activated, store any information traversing the system 100, or any combination thereof. Furthermore, the database 155 may be configured to process queries sent to it by any device in the system 100.

Operatively, the system 100 may improve an artificial respirator as shown in the following exemplary scenario. In the example scenario, the first user 101 may be an individual that requires the use of an artificial respirator 115 to support the first user's 101 breathing and/or lung functions. The first user 101 may place the respiration mask 126 on his face and secure the respiration mask 126 using the bands 127. The system 100 may obtain a first tension measurement from the tension sensor 128 of the respiration unit 125 when the respiration mask 126 is secured to the first user's 101 head and face. The first user 101 may then proceed to stretch the bands 127 to remove the respiration mask 126 from his face. When the bands 127 are stretched, the system 100 may obtain a second tension measurement from the tension sensor 128 of the respiration unit 125. The system 100 may determine a change in tension between the first and second tension measurements to determine if a threshold tension change has been satisfied. If the threshold tension change has been satisfied, the respiration mask 126 may be determined to have been removed from the first user 101 and one or more operations of the artificial respirator 115 may be suspended and/or reduced. The suspension of the one or more operations of the artificial respirator 115 may be overridden by the first user 101 and/or the caregiver of the first user 101 by inputting a sequence on the device controller 129, the peered-device controller 134, the second user device 111, the first user device 102, or any combination thereof.

As another example, the first user 101 may be sitting in room with the respiration mask 126 secured to his head. The NFC device 130 may be positioned on the respiration unit 125 and the NFC device 133 may be positioned on a necklace that the first user 101 is wearing. Initially, since the respiration mask 126 is secured to the first user 101, the determined distance between the NFC device 130 and the NFC device 133 may indicate that the NFC device 130 and the NFC device 133 are close together. This may indicate that the first user 101 is using the artificial respirator 115 to assist with breathing function. If, however, the first user 101 takes off the respiration mask 126, puts the respiration mask 126 on a table, and moves to another location in the first user's 101 home, the system 100 may re-determine the distance between the NFC device 133 and the NFC device 130. If the distance between the NFC device 133 and the NFC device 130 is at least a threshold distance, the system 100 may determine that the respiration mask 126 is no longer secured to the first user 101 and the system 100 may suspend and/or reduce one or more operations of the artificial respirator 115. If the distance is less than the threshold distance, the system 100 may perform no action and may continue to allow the artificial respirator 115 to function as it was. As a result, the system 100 may utilize the NFC devices 130, 133 to perform proximity detection to affect the operations of the artificial respirator 115.

As a further example, the first user 101 may have the respiration mask 126 secured to his head. The system 100 may obtain temperature measurements from the temperature sensors 131 when the respiration mask 126 is secured to the first user's 101 head. The first user 101 may proceed to remove the respiration mask 126 from the first user's head or the seal made by the respiration mask 126 on the user's face may be opened. At this point, the system 100 may obtain additional temperature measurements from the temperature sensors 131. If the additional temperature measurements fall outside a selected temperature range, this may indicate that the respiration mask 126 is not securely attached to the first user 101. For example, if the acceptable temperature range is between 95-100 degrees and if normal temperature measurements indicate a temperature reading of 98.6 degrees when the respiration mask 126 is secured to the first user 101, but the additional temperature measurements indicate a temperature of 80 degrees, this may indicate that the respiration mask 126 is not securely attached to the first user 101. The system 100 may then proceed to suspend and/or reduce one or more functions/operations of the artificial respirator 115. The functions/operations may be reactivated and/or increased at a selected time period, immediately based on using the device controller 129, the peered-device controller 134, the first user device 102, the second user device 111, or any combination thereof. Notably, the system 100 may incorporate any of the functionality and features described for the method 300 or as otherwise described herein.

Notably, as shown in FIG. 1, the system 100 may perform any of the operative functions disclosed herein by utilizing the processing capabilities of server 160, the storage capacity of the database 155, or any other component of the system 100 to perform the operative functions disclosed herein. The server 160 may include one or more processors 162 that may be configured to process any of the various functions of the system 100. The processors 162 may be software, hardware, or a combination of hardware and software. Additionally, the server 160 may also include a memory 161, which stores instructions that the processors 162 may execute to perform various operations of the system 100. For example, the server 160 may assist in processing loads handled by the various devices in the system 100, such as, but not limited to, receiving tension measurements from tension sensors that indicate the tension in a band supporting a respiration mask; determining whether a change in tension between tension measurements exceeds a threshold value; determining if a distance between a device positioned on a user and a device positioned on the respiration mask exceeds a threshold distance; determining if a temperature measurement received from a temperature sensor of the respiration mask is outside a selected temperature range; suspending functions of an artificial respirator coupled to the respiration mask; activating functions of the artificial respirator coupled to the respiration mask; receiving signals to activate and/or suspend functions of the artificial respirator; determining whether a sequence of inputs for suspending and/or reactivating a function of the artificial respirator have been received; determining whether a device controller or peered-device controller has provided signals to suspend or reactivate a function of the artificial respirator; receiving signals to activate and/or deactivate a microphone/speaker of the respiration mask; and performing any other suitable operations conducted in the system 100 or otherwise. In one embodiment, multiple servers 160 may be utilized to process the functions of the system 100. The server 160 and other devices in the system 100 may utilize the database 155 for storing data about the devices in the system 100 or any other information that is associated with the system 100. In one embodiment, multiple databases 155 may be utilized to store data in the system 100.

Although FIGS. 1-2 illustrate specific example configurations of the various components of the system 100 the system 100 may include any configuration of the components, which may include using a greater or lesser number of the components. For example, the system 100 is illustratively shown as including a first user device 102, a second user device 111, an artificial respirator 115, a power source 120, a respiration unit 125, a respiration mask 126, a head strap 127, a tension sensor 128, a device controller 129, an NFC device 130, a temperature sensor 131, a speaker/microphone 132, an NFC device 133, a peered device controller 134, a communications network 135, a switch 136, a server 140, a server 145, a server 160, and a database 155. However, the system 100 may include multiple first user devices 102, multiple second user devices 111, multiple artificial respirators 115, multiple power sources 120, multiple respiration units 125, multiple respiration masks 126, multiple head straps 127, multiple tension sensors 128, multiple device controllers 129, multiple NFC devices 130, multiple temperature sensors 131, multiple speakers/microphones 132, multiple NFC devices 133, multiple peered-device controllers 134, multiple communications networks 135, multiple switches 136, multiple servers 140, multiple servers 145, multiple servers 160, and multiple databases 155, or any number of any of the other components in the system 100. In certain embodiments, the apparatus 200 may include the artificial respirator 115, the power source 120, the respiration unit 125, the NFC device 133, the peered-device controller 134, any other device, or any combination thereof. Furthermore, in certain embodiments, substantial portions of the functionality and operations of the system 100 may be performed by other networks and systems that may be connected to system 100.

As shown in FIG. 3, an exemplary method 300 for improving an artificial respirator is schematically illustrated, and may include, at step 302, placing a respiration mask 126 of an artificial respirator 115 on a user, such as first user 101. In certain embodiments, the placing of the respiration mask 126 on the user may be performed by the first user 101, a caregiver of the first user 101, or any combination thereof. At step 304, the method 300 may include receiving, such as during a first time period, a first tension measurement that indicates tension in one or more bands 127 supporting the respiration mask 126. The first tension measurement may be taken when the respiration mask 126 is known to be secured to the first user 101. In certain embodiments, the first tension measurement may be obtained from the tension sensors 128 and may sent to and processed by the first user device 102, the second user device 111, the artificial respirator 115, the respiration unit 125, the server 140, the server 145, the server 160, the communications network 135, any combination thereof, or by utilizing any other appropriate program, network, system, or device.

At step 306, the method 300 may include receiving, during a second time period, a second tension measurement that indicates tension in one or more bands 127 supporting the respiration mask 126. In certain embodiments, the second tension measurement may be obtained from the tension sensors 128 and may sent to and processed by the first user device 102, the second user device 111, the artificial respirator 115, the respiration unit 125, the server 140, the server 145, the server 160, the communications network 135, any combination thereof, or by utilizing any other appropriate program, network, system, or device. At step 308, the method 300 may include determining if the change in tension between the first tension measurement and the second tension measurement exceeds a threshold. In certain embodiments, the change in tension may be determined by utilizing the tension sensors 128, the first user device 102, the second user device 111, the artificial respirator 115, the respiration unit 125, the server 140, the server 145, the server 160, the communications network 135, any combination thereof, or by utilizing any other appropriate program, network, system, or device.

If the change in tension does not exceed a threshold, this may indicate that the respiration mask 126 is still secured to the face of the first user 101 and/or that the respiration mask 126 has not changed its position enough to warrant further action. As such, the method 300 may revert back to step 306 to obtain additional tension measurements until changes in tension satisfy the threshold. If, at step 308, the change in tension between the first and second measurements does exceed the threshold, the method 300 may include, at step 310, suspending and/or reducing one or more functions of the artificial respirator 115. For example, the air pressure action performed by the artificial respirator 115 may be reduced or suspended altogether indefinitely or for a set period of time. In certain embodiments, the suspension and/or reducing of the functions of the artificial respirator 115 may be performed by utilizing the artificial respirator 115, the respiration unit 125, the server 140, the server 145, the server 160, the communications network 135, any combination thereof, or by utilizing any other appropriate program, network, system, or device. At step 312, the method 300 may include reactivating the function of the artificial respirator 115 after a set period of time, after the occurrence of a condition, based on receiving an input from the first user 102, or any combination thereof. In certain embodiments, the reactivation may be performed by utilizing the artificial respirator 115, the respiration unit 125, the server 140, the server 145, the server 160, the communications network 135, any combination thereof, or by utilizing any other appropriate program, network, system, or device.

At step 314, the method 300 may include determining a distance between a first device (e.g. NFC device 133) positioned on the first user 101 and a second device (e.g. NFC device 130) positioned on the respiration unit 125 and/or mask 126. In certain embodiments, the distance may be determined by utilizing the NFC device 130, the NFC device 133, the respiration unit 125, the server 140, the server 145, the server 160, the communications network 135, any combination thereof, or by utilizing any other appropriate program, network, system, or device. At step 316, the method 300 may include determining whether the distance between the first device and the second device exceeds a threshold distance. In certain embodiments, the determining may be performed by utilizing the NFC device 130, the NFC device 133, the respiration unit 125, the server 140, the server 145, the server 160, the communications network 135, any combination thereof, or by utilizing any other appropriate program, network, system, or device. If the distance between the first and second devices does not exceed the threshold distance, the method 300 may revert back to step 314 to take additional distance measurements until the threshold distance is satisfied. If the distance between the first and second devices does satisfy the threshold distance, the method 300 may include proceeding to step 310 to suspend and/or reduce one or more functions of the artificial respirator 115. The method 300 may then proceed to step 312 and may include reactivating the one or more functions of the artificial respirator 115 after a set period of time, after the occurrence of a condition, based on receiving an input from the first user 102, or any combination thereof.

At step 318, the method 300 may include receiving a temperature measurement from one or more temperature sensors 131 of the respiration mask 126. The temperature sensors 131 may measure the temperature at various points along the respiration mask 126, such as at the locations where the respiration mask 126 contacts the first user's 102 skin. In certain embodiments, the temperature measurements may be taken by utilizing the temperature sensors 131 and the temperature measurements may be sent to and processed by utilizing the artificial respirator 115, the respiration unit 125, the server 140, the server 145, the server 160, the communications network 135, any combination thereof, or by utilizing any other appropriate program, network, system, or device. At step 320, the method 300 may include determining if the temperature measurement is outside a selected temperature range. In certain embodiments, the determining may be performed by utilizing the artificial respirator 115, the respiration unit 125, the server 140, the server 145, the server 160, the communications network 135, any combination thereof, or by utilizing any other appropriate program, network, system, or device.

If the temperature measurement is not outside the selected temperature range, the method 300 may revert back to step 318 and continue to take temperature measurements until a temperature measurement outside the temperature range occurs. If the temperature measurement is outside the temperature range, the method 300 may include proceeding to step 310 and suspending and/or reducing one or more functions of the artificial respirator 115. The method 300 may then proceed to step 312 and may include reactivating the one or more functions of the artificial respirator 115 after a set period of time, after the occurrence of a condition, based on receiving an input from the first user 102, or any combination thereof. Notably, the method 300 may further incorporate any of the functionality and features as described for system 100, the apparatus 200, or as otherwise described herein.

Notably, the system 100, the apparatus 200, and methods disclosed herein may include additional functionality and features. For example, in certain embodiments, the system 100, the apparatus 200, and methods may include generating and transmitting alerts whenever a function of the artificial respirator 115 is suspended and/or reactivated, whenever temperature measurements exceed a threshold, whenever changes in tension measurements exceed a threshold, and/or whenever the distance between the NFC devices 133, 130 exceed a threshold distance. The alerts may include information identifying the user using the artificial respirator, medical health records of the user, an identification of what functions of the artificial respirator 115 have been suspended and/or reactivated, an identification of a breathing rate of the user, an identification of the pressure of the air provided by the artificial respirator 115, temperature measurements from the temperature sensors 131, tension measurements from the tension sensors 128, any other information traversing the system 100, or any combination thereof. The alerts may be transmitted to the second user device 111 of the second user 110, who may be a caregiver, so as to alert the second user 110 of functioning of the artificial respirator 115.

In certain embodiments, the alerts generated by the artificial respirator to be ramped up over time. In traditional artificial respirators, whenever the respirator detects insufficient back-pressure to the respiration mask, the respirator may constantly beep or output a sound. Often times, slight changes in orientation of the respiration mask may cause small air gaps with respect to the user's skin, which then affect the back-pressure measurements recorded by the respirator machine. In response, the respirator machines often beep loudly so that a caregiver may rush to the user and save them. That being said, such beeps and sounds made by traditional respirators typically occur several times a minute, for twenty-four hours a day. This may cause the caregiver to become used to the sound since the sound is almost always there and the caregiver may not think there is an emergency. In order to prevent such a scenario, the back-pressure to the respiration mask 126 may be detected by the system 100 (e.g. by the artificial respirator 115), and, if the back-pressure is below a threshold, a low-volume beeping or other sound may be output at a first frequency or periodicity. In certain embodiments, the sounds may be output by the artificial respirator 115 itself or by other components of the system 100. If the back-pressure remains too low for a selected duration, the volume of the beeping or other sound may gradually be increased until eventually the sound is output at a target volume, frequency, and/or periodicity. When the target volume, frequency and/or periodicity occur, the event (i.e. back-pressure being too low) may be flagged by the system 100. Instead of the incessant, maximum-volume beeping that occurs in current respirator devices, the functionality provided by the system 100 would replace the loud beeps with quieter beeps that ramp up in volume only if needed and ultimately change in order to catch the attention of the caregiver.

In certain embodiments, upon receiving one or more alerts, the second user 110 may remotely override any faulty suspensions and/or reactivations made with respect to the functions of the artificial respirator 115, such as by selecting an override option in an application executing on the second user device 111 that is communicatively linked with the apparatus 200. In certain embodiments, the alerts may be stored in a health record associated with the user so that the patient's health may be monitored to determine any deviations with respect to his or her medical history and/or deviations with respect to normal health conditions. In certain embodiments, temperature measurements may be recorded over time to determine an average temperature and alarms may be set, such as via an application executing on the first and second user devices 102, 111, to go off when temperature measurements deviate from the average temperature.

In further embodiments, the time period for suspending and/or reactivating a function of the artificial respirator may be configurable by the first and/or second user 101, 110, such as via an application executing on the first and second user devices 102, 111. For example, the first user 101 may set that a suspension of the air pressure action of the artificial respirator 115 should only last 5 minutes. In certain embodiments, the first user 101 may also set that even during a suspension period, that the air pressure action (or other function) should periodically be activated for a few time intervals to ensure safety. The application may also allow the first and second users 101, 110 to configure any of the functions of the artificial respirator 115, the respiration unit 125, any other device in the system 100, or any combination thereof. In certain embodiments, the application may track how frequently the various functions are activated and/or suspended. In certain embodiments, the application may output the alerts and/or alarms, and may be configured to alert caregivers and/or healthcare providers. The application may also be utilized to deactivate functions of the system 100. In certain embodiments, the system 100, the apparatus 200, and methods may include providing a notification of an incoming call to a mobile device of the user and automatically suspending one or more functions of the artificial respirator 115 when the incoming call is accepted on the mobile device by the user.

Figure 4:
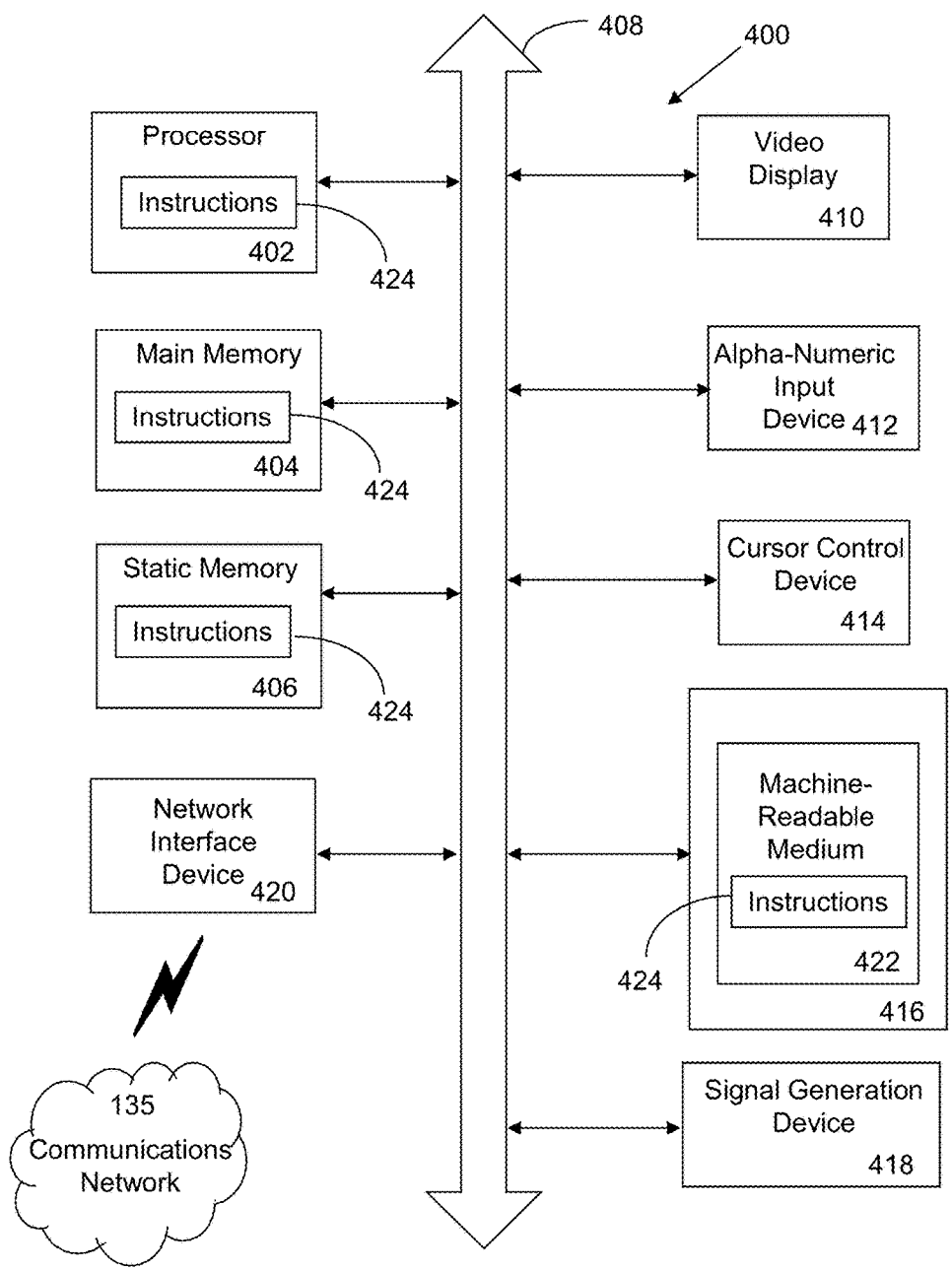
FIG. 4 is a schematic diagram of a machine in the form of a computer system within which a set of instructions, when executed, may cause the machine to perform any one or more of the methodologies or operations of the systems, apparatuses, and methods for improving an artificial respirator.

Referring now also to FIG. 4, at least a portion of the methodologies and techniques described with respect to the exemplary embodiments of the system 100 can incorporate a machine, such as, but not limited to, computer system 400, or other computing device within which a set of instructions, when executed, may cause the machine to perform any one or more of the methodologies or functions discussed above. The machine may be configured to facilitate various operations conducted by the system 100. For example, the machine may be configured to, but is not limited to, assist the system 100 by providing processing power to assist with processing loads experienced in the system 100, by providing storage capacity for storing instructions or data traversing the system 100, or by assisting with any other operations conducted by or within the system 100.

In some embodiments, the machine may operate as a standalone device. In some embodiments, the machine may be connected (e.g., using communications network 135, another network, or a combination thereof) to and assist with operations performed by other machines and systems, such as, but not limited to, the first user device 102, the second user device 111, the artificial respirator 115, the respiration unit 125, the device controller 129, the NFC device 130, the temperature sensor 131, the speaker/microphone 132, the NFC device 133, the peered device controller 134, the server 140, the server 145, the database 155, the server 160, any other device or sensor, or any combination thereof. The machine may be connected with any component in the system 100. In a networked deployment, the machine may operate in the capacity of a server or a client user machine in a server-client user network environment, or as a peer machine in a peer-to-peer (or distributed) network environment. The machine may comprise a server computer, a client user computer, a personal computer (PC), a tablet PC, a laptop computer, a desktop computer, a control system, a network router, switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The computer system 400 may include a processor 402 (e.g., a central processing unit (CPU), a graphics processing unit (GPU, or both), a main memory 404 and a static memory 406, which communicate with each other via a bus 408. The computer system 400 may further include a video display unit 410, which may be, but is not limited to, a liquid crystal display (LCD), a flat panel, a solid state display, or a cathode ray tube (CRT). The computer system 400 may include an input device 412, such as, but not limited to, a keyboard, a cursor control device 414, such as, but not limited to, a mouse, a disk drive unit 416, a signal generation device 418, such as, but not limited to, a speaker or remote control, and a network interface device 420.

The disk drive unit 416 may include a machine-readable medium 422 on which is stored one or more sets of instructions 424, such as, but not limited to, software embodying any one or more of the methodologies or functions described herein, including those methods illustrated above. The instructions 424 may also reside, completely or at least partially, within the main memory 404, the static memory 406, or within the processor 402, or a combination thereof, during execution thereof by the computer system 400. The main memory 404 and the processor 402 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine-readable medium 422 containing instructions 424 so that a device connected to the communications network 135, another network, or a combination thereof, can send or receive voice, video or data, and to communicate over the communications network 135, another network, or a combination thereof, using the instructions. The instructions 424 may further be transmitted or received over the communications network 135, another network, or a combination thereof, via the network interface device 420.

While the machine-readable medium 422 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that causes the machine to perform any one or more of the methodologies of the present disclosure.

The terms "machine-readable medium," "machine-readable device, or "computer-readable device" shall accordingly be taken to include, but not be limited to: memory devices, solid-state memories such as a memory card or other package that houses one or more read-only (nonvolatile) memories, random access memories, or other re-writable (volatile) memories; magneto-optical or optical medium such as a disk or tape; or other self-contained information archive or set of archives is considered a distribution medium equivalent to a tangible storage medium. The "machine-readable medium," "machine-readable device," or "computer-readable device" may be non-transitory, and, in certain embodiments, may not include a wave or signal per se. Accordingly, the disclosure is considered to include any one or more of a machine-readable medium or a distribution medium, as listed herein and including art-recognized equivalents and successor media, in which the software implementations herein are stored.

The illustrations of arrangements described herein are intended to provide a general understanding of the structure of various embodiments, and they are not intended to serve as a complete description of all the elements and features of apparatus and systems that might make use of the structures described herein. Other arrangements may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Thus, although specific arrangements have been illustrated and described herein, it should be appreciated that any arrangement calculated to achieve the same purpose may be substituted for the specific arrangement shown. This disclosure is intended to cover any and all adaptations or variations of various embodiments and arrangements of the invention. Combinations of the above arrangements, and other arrangements not specifically described herein, will be apparent to those of skill in the art upon reviewing the above description. Therefore, it is intended that the disclosure not be limited to the particular arrangement(s) disclosed as the best mode contemplated for carrying out this invention, but that the invention will include all embodiments and arrangements falling within the scope of the appended claims.

The foregoing is provided for purposes of illustrating, explaining, and describing embodiments of this invention. Modifications and adaptations to these embodiments will be apparent to those skilled in the art and may be made without departing from the scope or spirit of this invention. Upon reviewing the aforementioned embodiments, it would be evident to an artisan with ordinary skill in the art that said embodiments can be modified, reduced, or enhanced without departing from the scope and spirit of the claims described below.

We claim:

1. A system, comprising:
   a memory that stores instructions; and
   a processor that executes the instructions to perform operations, the operations comprising:
   receiving, during a first time period, a first tension measurement from a tension sensor positioned on a respiration mask, wherein the first tension measurement indicates tension in a band that supports the respiration mask while the respiration mask is positioned on a user;
   receiving, during a second time period, a second tension measurement from the tension sensor, wherein the second tension measurement indicates tension in the band;
   determining that a change in tension between the first tension measurement and the second tension measurement exceeds a first threshold value,
   suspending a function of an artificial respirator coupled to the respiration mask; and
   reactivating the function of the artificial respirator for a predetermined duration during a suspension time period associated with suspending the function of the artificial respirator.

2. The system of claim 1, wherein the operations further comprise determining a distance between a first near-field communication device positioned on the user and a second near-field communication device positioned on the respiration mask.

3. The system of claim 2, wherein the operations further comprise suspending, if the distance between the first near-field communication device positioned on the user and the second near-field communication device positioned on the respiration mask exceeds a second threshold value, the function of the artificial respirator coupled to the respiration mask.

4. The system of claim 1, wherein the operations further comprise receiving a temperature measurement from a temperature sensor of the respiration mask.

5. The system of claim 4, wherein the operations further comprise suspending, if the temperature measurement is outside a selected temperature range, the function of the artificial respirator coupled to the respiration mask.

6. The system of claim 1, wherein the operations further comprise receiving a signal indicating activation of a switch of the respiration mask, and wherein the operations further comprise suspending the function of the artificial respirator coupled to the respiration mask when the signal is received.

7. The system of claim 6, wherein the operations further comprise activating a microphone and a speaker of the respiration mask when the signal is received.

8. The system of claim 1, wherein the operations further comprise receiving a back-pressure measurement associated with back-pressure to the respiration mask.

9. The system of claim 8, wherein the operations further comprise outputting an alert at a first frequency if the back-pressure measurement is lower than a second threshold value.

10. The system of claim 9, wherein the operations further comprise outputting the alert at a second frequency if subsequent back-pressure measurements remain lower than the second threshold value for a selected time period.

11. The system of claim 1, wherein the operations further comprise transmitting a notification to a mobile device indicating that the function of the artificial respirator has been suspended.

12. The system of claim 1, wherein the operations further comprise receiving a notification of an incoming call to a mobile device of the user, and wherein the operations further comprise suspending the function of the artificial respirator when the incoming call is accepted on the mobile device.

13. The system of claim 1, wherein the operations further comprise receiving a sequence of inputs from a device controller associated with the artificial respirator, and wherein the operations further comprise suspending the function of the artificial respirator if the sequence of inputs matches a predetermined sequence of inputs for suspending the function.

14. A method, comprising:
receiving, during a first time period, a first tension measurement from a tension sensor positioned on a respiration mask, wherein the first tension measurement indicates tension in a band that supports the respiration mask while the respiration mask is positioned on a user;
receiving, during a second time period, a second tension measurement from the tension sensor, wherein the second tension measurement indicates tension in the band;
determining, by utilizing instructions from a memory that are executed by a process, that a change in tension between the first tension measurement and the second tension measurement exceeds a first threshold value,
suspending a function of an artificial respirator coupled to the respiration mask; and
reactivating the function of the artificial respirator for a predetermined duration during a suspension time period associated with suspending the function of the artificial respirator.

15. The method of claim 14, further comprising suspending the function of the artificial respirator upon receiving a signal from an application executing on a mobile device of the user, wherein the signal indicates that the function is to be suspended.

16. The method of claim 14, further comprising outputting an alert when the function is suspended.

17. The method of claim 14, further comprising determining a distance between a first near-field communication device positioned on the user and a second near-field communication device positioned on the respiration mask.

18. The method of claim 17, further comprising suspending, if the distance between the first near-field communication device positioned on the user and the second near-field communication device positioned on the respiration mask exceeds a second threshold value, the function of the artificial respirator coupled to the respiration mask.

19. The method of claim 14, further comprising receiving a notification of an incoming call to a mobile device of the user, and further comprising suspending the function of the artificial respirator when the incoming call is accepted on the mobile device.

20. A computer-readable device comprising instructions, which, when loaded and executed by a processor, cause the processor to perform operations, the operations comprising:
receiving, during a first time period, a first tension measurement from a tension sensor positioned on a respiration mask, wherein the first tension measurement indicates tension in a band that supports the respiration mask while the respiration mask is positioned on a user;
receiving, during a second time period, a second tension measurement from the tension sensor, wherein the second tension measurement indicates tension in the band;
determining that a change in tension between the first tension measurement and the second tension measurement exceeds a first threshold value;
suspending a function of an artificial respirator coupled to the respiration mask; and
reactivating the function of the artificial respirator for a predetermined duration during a suspension time period associated with suspending the function of the artificial respirator.

* * * * *